(12) United States Patent
Brainard, II

(10) Patent No.: US 8,460,196 B2
(45) Date of Patent: Jun. 11, 2013

(54) METHOD AND APPARATUS FOR MONITORING BRAIN ACTIVITY

(75) Inventor: Edward C. Brainard, II, Marion, MA (US)

(73) Assignee: Atlantis Limited Partnership, Marion, MA (US)

(*) Notice: Subject to any disclaimer, the term of this patent is extended or adjusted under 35 U.S.C. 154(b) by 1048 days.

(21) Appl. No.: 12/475,156

(22) Filed: May 29, 2009

(65) Prior Publication Data

US 2010/0305456 A1 Dec. 2, 2010

(51) Int. Cl.
*A61B 5/02* (2006.01)

(52) U.S. Cl.
USPC .......................................................... 600/483

(58) Field of Classification Search
USPC ........................................ 600/340, 483, 544
See application file for complete search history.

(56) References Cited

U.S. PATENT DOCUMENTS

| | | | |
|---|---|---|---|
| 6,615,065 B1* | 9/2003 | Barrett et al. | 600/340 |
| 2004/0059201 A1* | 3/2004 | Ginsberg | 600/300 |
| 2005/0222502 A1* | 10/2005 | Cooper | 600/323 |
| 2007/0135694 A1* | 6/2007 | Sato et al. | 600/328 |
| 2008/0021332 A1* | 1/2008 | Brainard, III | 600/483 |

* cited by examiner

*Primary Examiner* — Navin Natnithithadha
*Assistant Examiner* — Etsub Berhanu
(74) *Attorney, Agent, or Firm* — Young & Thompson

(57) ABSTRACT

Method for monitoring brain activity. Left and right cardiac pulse signals are detected at bilateral locations on a body for a selected number of cardiac cycles. Computing apparatus computes the standard deviation of the left and right pulse signals for the selected number of cardiac cycles. The standard deviations are normalized on the computing apparatus by dividing the left and right standard deviations by the mean of the left and right pulse signals computed over the selected number of cardiac cycles to produce a left and a right Coefficient of Variation of the pulse signals. A Bilateral Pulse Index is generated from the left and right Coefficients of Variation. The Bilateral Pulse Index relates to brain activity. Cardiac pulse signals from a single location on the body may be utilized in some embodiments.

11 Claims, 7 Drawing Sheets

METHOD AND APPARATUS FOR MONITORING BRAIN ACTIVITY

BACKGROUND OF THE INVENTION

This invention relates to method and apparatus for monitoring brain activity and more particularly to method and apparatus that assesses brain activity by measuring cardiac pulse, preferably bilaterally, on a body.

It is desirable to be able to monitor brain activity such as for determining a sleep threshold or to determine "awareness" during surgery or to adjust dosage of anesthesia agents. Michael Airken, et al., in "Anesthesia Awareness and the Bispectral Index," *The New England Journal of Medicine*, Mar. 13, 2008, vol. 358, No. 11, performed tests to determine the effectiveness of bilateral spectral analysis, BIS, for use during surgery to determine if a patient was experiencing "awareness." Their analysis indicates that the technique does not provide a reliable method for this purpose, thereby leaving a vacuum for this type of measurement.

N. A. Laren, et al., in "Brain Function and Blood Flow," *Scientific American*, October, 1978, made brain imaging measurements using positron emission tomography. These measurements provide observations of areas in the brain where mental activity was taking place during the execution of specific tasks. The method also provided estimates of blood flow to the brain. In general, a doubling in blood flow can be expected when a subject is carrying out active mental tasks. John Allen, et al., in "Similarity in Bilateral Photo-Plethysmographic Peripheral Pulse Wave Characteristics at Ears, Thumbs and Toes," *Physio. Meas.* 21 (2000) 369-377, reported making bilateral pulse measurements at the earlobes. His work did not report changes in his measurements with mental activity.

It is an object of the present invention to measure cardiac pulses, preferably bilaterally, at the earlobes, forehead, or carotid artery at the neck to assess brain activity to determine, for example, a sleep threshold or to determine awareness during surgery.

SUMMARY OF THE INVENTION

The method according to a first aspect of the invention for monitoring brain activity includes detecting cardiac pulse signals at a location on a body for a selected number of cardiac cycles. The variance or standard deviation of the pulse signals is computed on computing apparatus for the selected number of cardiac cycles. The variance or standard deviation is processed to produce a coefficient of variation of the pulse signals and a pulse index is generated from the coefficient of variation wherein the pulse index relates to brain activity.

In another aspect, the method for monitoring brain activity includes detecting left and right cardiac pulse signals at bilateral locations on a body for a selected number of cardiac cycles. The variance or standard deviation of the left and right pulse signals is computed for the selected number of cardiac cycles. The variance or standard deviation is normalized on the computing apparatus to produce a left and right coefficient of variation (CV) of the pulse signals. A bilateral pulse index (BPI) is generated from the left and right coefficients of variation by combining them mathematically, wherein the BPI relates to brain activity.

The method according to yet another aspect of the invention for monitoring brain activity includes detecting left and right cardiac pulse signals at bilateral locations on a body for a selected number of cardiac cycles. The standard deviation or variance of the left and right pulse signals are computed on computing apparatus for the selected number of cardiac cycles. The standard deviation of the left and right pulse signals are normalized on the computing apparatus by dividing the left and right standard deviations by the mean of the left and right pulse signals, respectively, computed over the selected number of cardiac cycles to produce a left and a right Coefficient of Variation (CV) of the pulse signals. A Bilateral Pulse Index (BPI) from the left and right coefficients of variation are generated according to the equation BPI=((Left CV+Right CV)/2)+(Absolute (Left CV−Right CV)). The BPI index relates to brain activity. In a preferred embodiment, the bilateral locations are the left and right earlobes. Other suitable locations for bilateral monitoring are the left and right portions of the forehead or left and right carotid arteries at the neck. Suitable brain activity for monitoring is the sleep state or level or awareness under anesthesia. It is preferred that the pulse signals are detected by plethysmographic sensors or oximeter sensors.

BRIEF DESCRIPTION OF THE DRAWING

FIG. 1b is the Fast Fourier Transform, FFT, of the pulse shown in FIG. 1a.

FIG. 4b is a plot of Bilateral Pulse Index vs. time showing the last portion of the surgical procedure relating to FIG. 4a.

DESCRIPTION OF THE PREFERRED EMBODIMENT

Figure 1B:
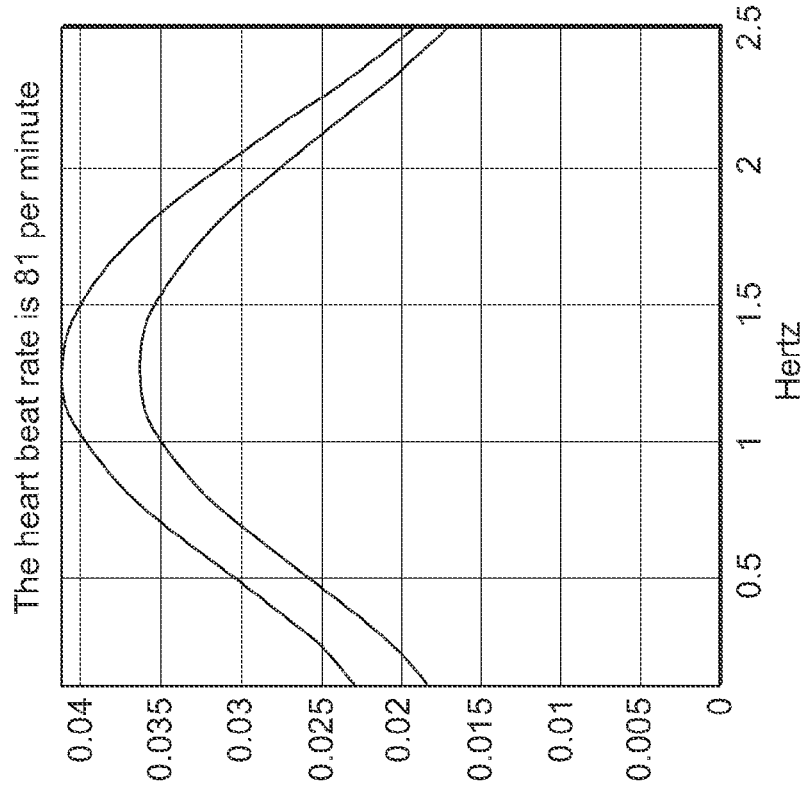

I have discovered that I can infer left and right brain activity by simultaneously monitoring the cardiac pulse on the earlobes of subjects and at other bilateral locations. I call this procedure the Bilateral Pulse Method. To date I have used infrared plethysmographic (Pleth) sensors for this monitoring. I have employed the sensors not only on earlobes, but have also used them on the forehead and in the area of the carotid artery. I have utilized MatLab software that allows for the accurate processing of pulse signals using digital signal processing, statistical processing, and convenient graphing to display data including sequential pulses as they are recorded. While the most reliable signal to use for awareness detection is the BPI that uses the left and right CV, there can be times when only one signal from a single location is available. Thus, cardiac pulse signals at a single location on the body can be used for awareness detection.

The present invention is based on the following observations. The external carotid arteries are branches of the carotid arteries. These feed blood to the jaw, face and scalp, including the ears. The principle of the present invention is based on the fact that measurements of blood flow at such areas as the earlobes and the forehead directly reflect the blood flow to the brain through the carotid arteries. It appears that blood flow to the earlobes and forehead relate to blood flow to the brain. Thus, a measurement of blood flow at the earlobes appears to be a relative measurement of the blood flow to the brain. In addition, simultaneous measurement of both earlobes gives a measurement of differential functioning of the left and right brain.

It has been observed during experiments of the bilateral pulse method disclosed herein that a subject will tend to modulate the blood flow to the left and right hemispheres of the brain. It is not just a gradual change of flow following the cardiac pulse. The heart is the primary pump for blood. The aorta acts as a secondary pump due to its wall expending the energy previously stored from the contraction of the heart thereby forcing the blood onward when the heart is resting. When mental activity occurs above rest levels, the blood supply to the brain significantly increases. This level expends considerable total body energy and is conserved to be used only as needed. Thus this modulation of the blood flow to the brain is the process by which this energy is used only as needed. This modulation generates a change of variance in the cardiac pulse data which is easily measured and from which the Bilateral Pulse Index is calculated.

My hypothesis for the operation of the invention disclosed herein is based on a recent explanation of consciousness proposed by Koch, et al., "How Does Consciousness Happen?", *Scientific American*, October, 2007. They describe consciousness as based on an interrelated operation of past, present, and future cognitive areas of the brain when functioning in harmony. This interrelationship means that these areas are interconnected and function as an entire system. During unconsciousness the interconnecting communication pathways are opened. Sleep produces this same breaking of the communication pathways. Once the pathways are opened, the need for blood flow is minimized due to less brain activity.

During early experiments the procedure for monitoring left and right brain activity has been to ask the test subject first to relax. This was necessary since the readings of the pulse magnitudes are affected by the placement of the sensor, skin color, thickness of tissue, and circulation of blood in the test area. Temperature can also affect the output since the subject will limit blood flow to extremities in a colder environment. Once the subject relaxes, the left and right magnitudes must be normalized to remove any difference, or balanced by moving the sensors. The assumption is that by relaxing the left and right hemispheres, the subject goes into minimized mental activity and the two hemispheres should have the same activity. However, measuring magnitude has not led to a faithful analysis of left and right hemisphere activity since there are other sources of magnitude change that are not directly related to hemisphere activity such as sensor movement.

I have observed that when a subject is fully relaxed, the standard deviation of the cardiac pulse signal at the earlobes and forehead will reach a minimum. I have deduced that when a subject is asleep, the standard deviation will also minimize further. The change in standard deviation from the relaxed state to active mental activity produces a significant signal to analyze, but it is affected by sensor placement and shift in position which are commonly encountered. To overcome this problem, I have normalized the standard deviation by dividing it by the mean of the data computed over the same sample length as the standard deviation. This computation provides the Coefficient of Variation, CV, of the sample. By analyzing the CV instead of magnitude, I have developed a monitoring method that is insensitive to sensor placement and movement. This monitoring technique has led to sleep tests and the projection that the monitoring of cardiac pulse CV reduction at the earlobes, forehead or at the carotid arteries may play a role in determining if a patient is fully anesthetized during surgery.

I will now describe the methods underlying this invention and experiments I have conducted. During anesthesia operating room experiments I have used two Masimo LNCS TC-1 Tip Clip oximeter sensors placed on the earlobes of the test subjects. Measurements can also be made on the forehead using readily available sensors. The outputs of these sensors were fed into linear AC amplifiers with a band pass from 0.28 to 10 Hz at the −3 dB point. The amplifiers were adjusted to give a one volt peak-to-peak output to an A/D type USB-1208 FS, manufactured by the Measurement Computer Corporation. This unit digitized the cardiac pulse outputs from the Masimo sensors at 2 kHz with a 12 bit resolution.

This digital serial stream of data was passed to a laptop computer running Windows XP. MatLab processing software was used to separate individual pulses from the data stream. Each pulse was processed with a Fast Fourier Transform and the peak magnitudes at the fundamental frequency of the left and right sensors were obtained. A running standard deviation of the digitally filtered pulse data was performed and then it was normalized by dividing the standard deviation by the mean computed over the same sample length. This resulting Coefficient of Variation, CV, data was plotted on the computer display. During post processing of an Excel file a new statistic was computed called the Bilateral Pulse Index, BPI, following the procedure listed below.

$$BPI = ((Left\ CV + Right\ CV)/2) + (Absolute(Left\ CV - Right\ CV)).$$

This Bilateral Pulse Index is used to provide a single number to evaluate the depth of sleep or anesthesia. This index is also very sensitive to a sensor giving an abnormal output. The algorithm is sensitive to dissimilarities between the left and right CVs by weighting the difference greater than the mean.

Figure 1A:
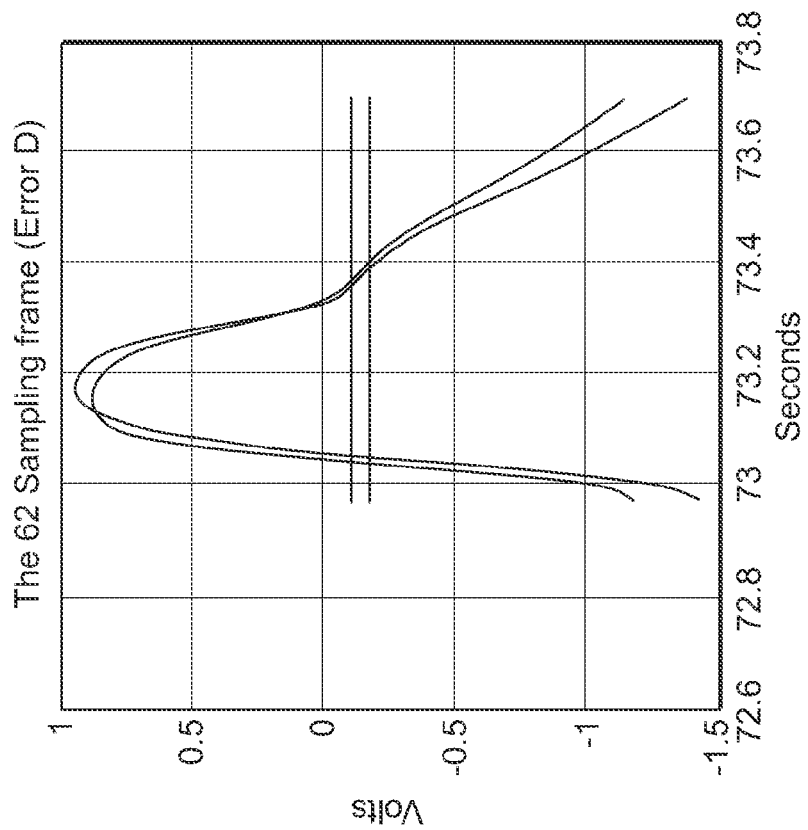
FIG. 1a is a graph of voltage vs. time for individual pulses as they are extracted from a data stream.
Figure 1C:
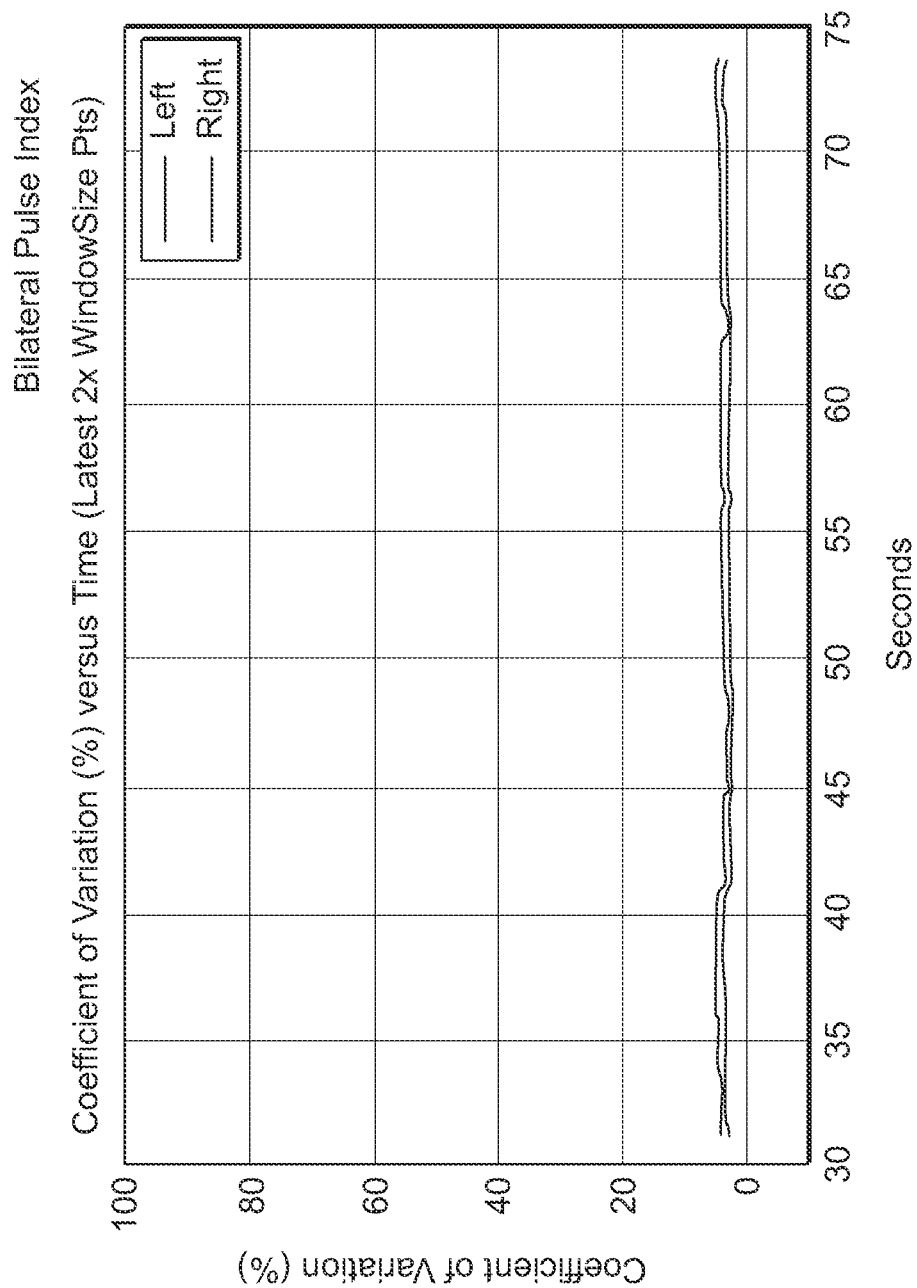
FIG. 1c is a graph of Coefficient of Variation in percent vs. time for bilateral pulses.

With reference now to the drawing, FIGS. 1*a*, 1*b* and 1*c* show the screen presentation for the bilateral pulse system disclosed herein. FIG. 1*a* shows individual pulses as they are extracted from the data stream. FIG. 1*b* shows the Fast Fourier Transform of the pulse shown in FIG. 1*a*. FIG. 1*c* shows the Coefficient of Variation, CV, of the left and right channels. It is noted that there is considerable control of the number of data samples that are used in an experimental run. All data processing in this application has been done using n=30. The averaging of multiple pulses is also available. All data reduction for the experiments described herein has used single pulses without any averaging.

The sleep experiments were carried out by having subjects lie supine on a bed with a soft pillow under their head. Lights were turned out in the room so that the only illumination was the laptop computer screen which provided enough light for the technician to make measurements and take notes. The computer screen was facing away from the subject to prevent distraction.

The anesthesia experiments were conducted in an operating room environment with the patient lying supine with a pillow under his or her head. The bilateral pulse experimental apparatus was placed on a dolly and positioned about eight feet diagonally from the head of the patient. The apparatus for the anethesiologist was on the other side of the patient diagonally from the head. The sensors were placed on the earlobes of the patient as soon as the patient was rolled into the operating room, but the patient had been mildly sedated before being brought to the operating room. Data was recorded during the full period of the operation in 20 minute segments.

The sensors were cleaned with isopropyl alcohol. The skin surfaces to which the sensors were attached were also cleaned. The use of the alcohol aids in preventing the sensors from slipping once placed in position.

The present methodology that uses the Coefficient of Variation and its derivative, the Bilateral Pulse Index, can be used without adjustments. It is essentially self-adjusting to the physiological conditions.

To date, I have run four sleep experiments of 21, 47, 119, and 192 minutes. I have found that the bilateral cardiac pulse CV measured at the earlobes reduces to a minimum with beginning of deep sleep. The reduction is less for a nap of 20-60 minutes, but still there is a measurable reduction. The deep sleep experiments have helped me establish a sleep threshold of 7.0 percent CV, which I am using for the anesthesia experiments. Based on the sleep experiments, I have used the Bilateral Pulse method disclosed herein in the operating room with success.

Figure 2A:
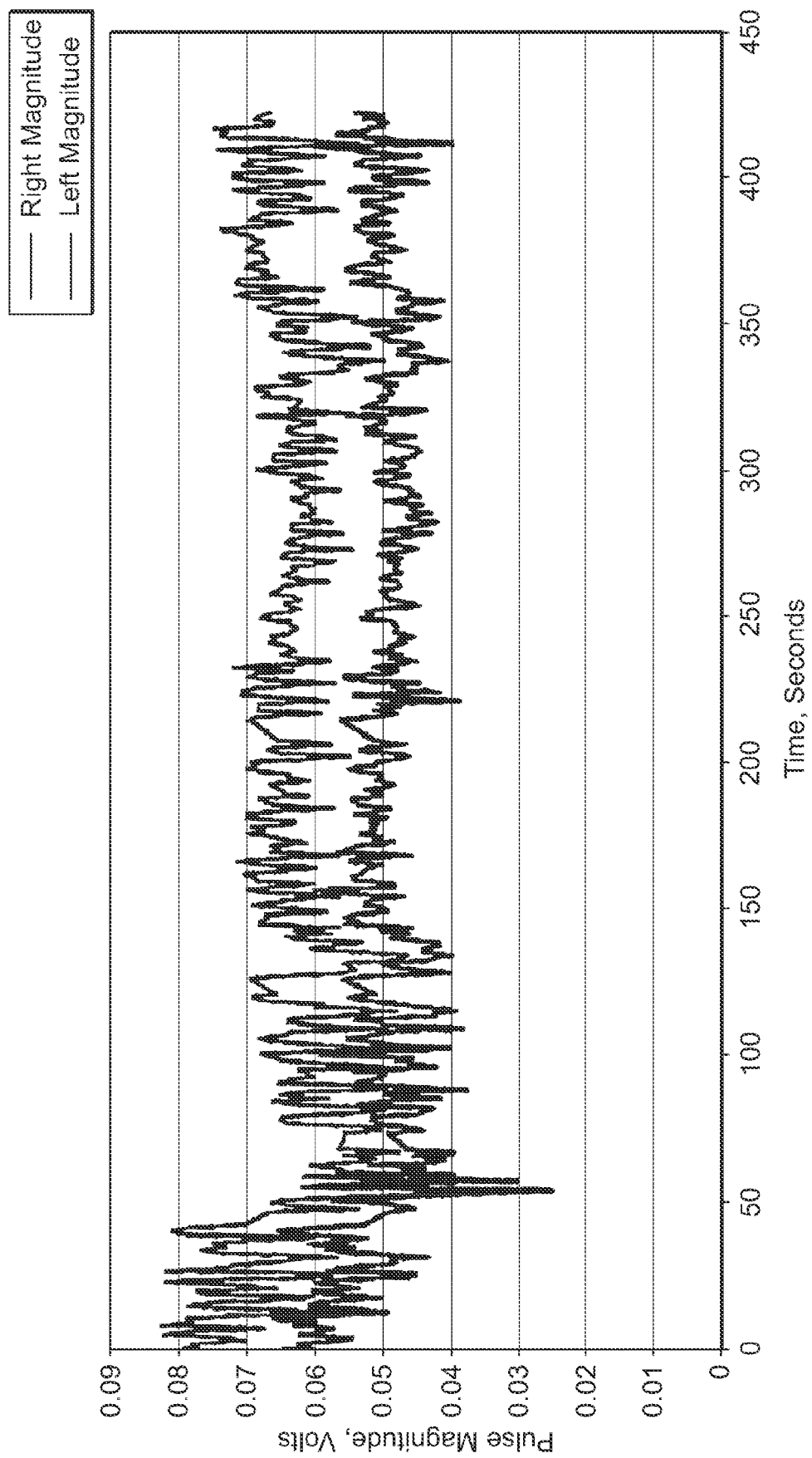
FIG. 2a is a graph of pulse magnitude vs. time for left and right measurements.
Figure 2B:
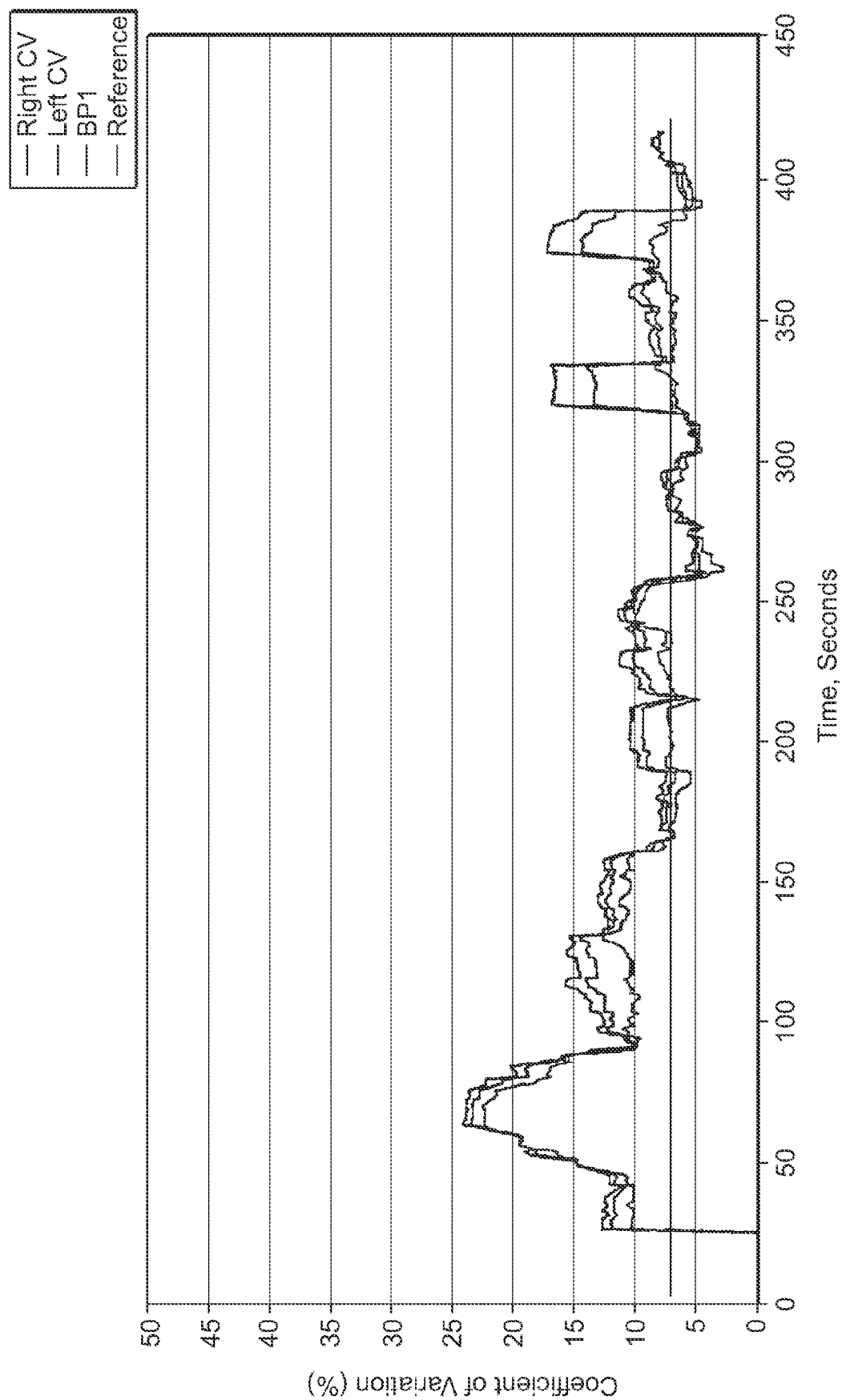
FIG. 2b is a graph of Coefficient of Variation in percent vs. time for right Coefficient of Variation, left Coefficient of Variation, and the Bilateral Pulse Index.
Figure 3:
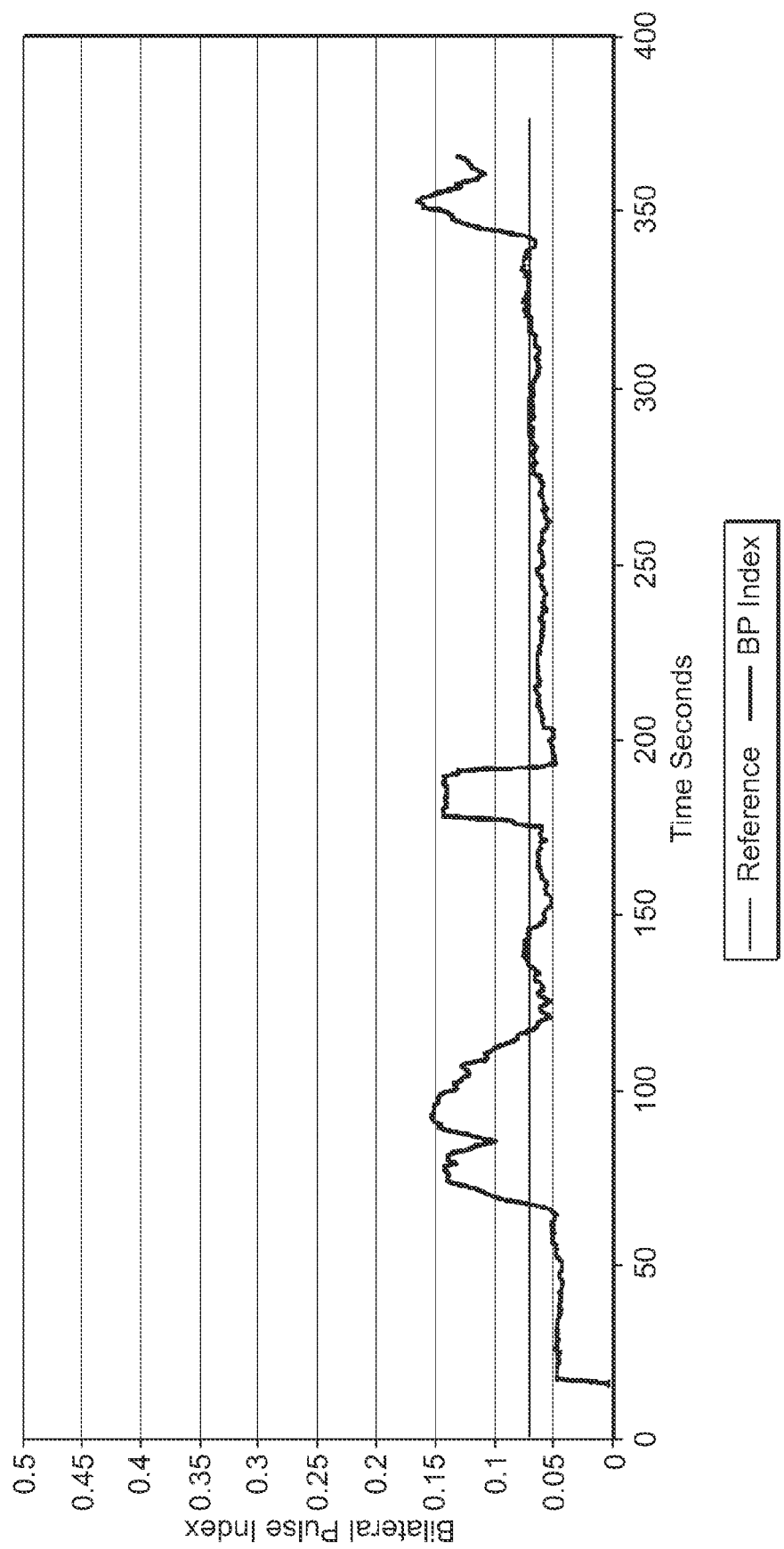
FIG. 3 is a graph of Bilateral Pulse Index vs. time for a sleeping subject.

FIGS. 2-4, discussed below, are provided to show the results obtained using the Bilateral Pulse method of the invention during mental activity, sleep, and anesthesia. FIG. 2a shows right and left pulse magnitude as a function of time while FIG. 2b shows the left and right Coefficient of Variation, CV, and the Bilateral Pulse Index, BPI. These plots were taken during a period when a subject was taking a test which required the viewing of a two-dimensional plane figure and trying to match it to one of five three-dimensional shapes. One shape was the result obtained after folding up the plane figure. Note the straight line at a BPI of 7.0 percent. It has been previously determined that below a BPI of 7.0 percent the subject would be asleep. In this experiment the subject was mentally active and became more active as the experiment continued. The shift in data at about 310 and 450 seconds are caused by noise in the data. A single spike in the data will shift the data for 30 pulses since the BPI is calculated with a 30 pulse sample. That data has only been modified to remove single data spikes that exceed three standard deviations. The automatic removal of more complex noise could be executed in software. The plotting of CV along with the BPI allows the observer to evaluate the performance of the BPI algorithm which has been described above. The BPI faithfully follows CV and is very sensitive to large differences between them which is considered a sign of mental activity.

FIG. 3 shows data from a sleeping subject. There is a data shift at about 190 seconds due to noise. It was observed that the subject was in deep sleep from about 200-300 seconds. This sleep experiment lasted about 2.5 hours. The plot in FIG. 3 was obtained during the end of the experiment. The subject was observed to go into deep sleep and out periodically. The data between 80-135 seconds is such an arousal period.

Figure 4A:
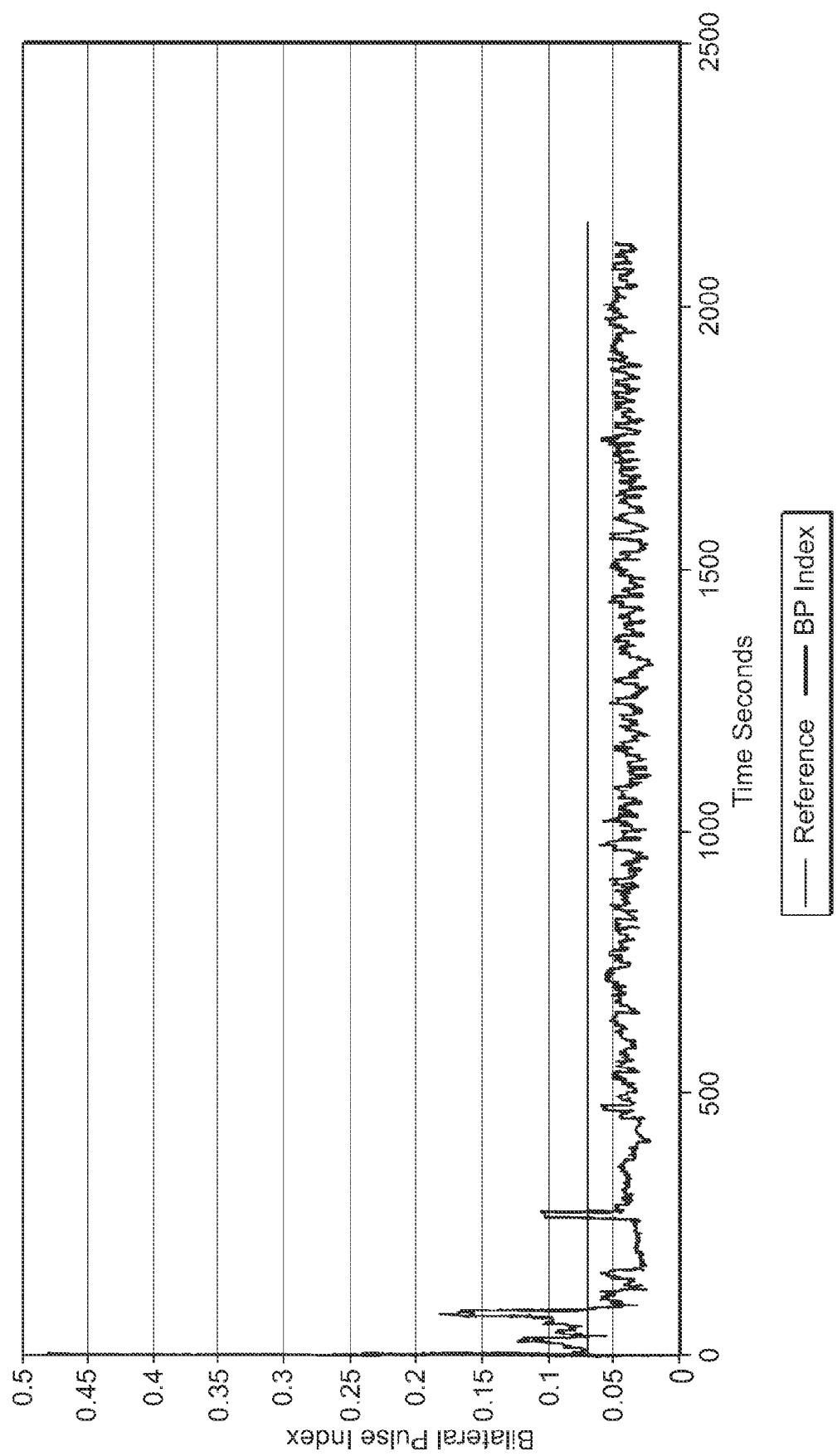
FIG. 4a is a graph of Bilateral Pulse Index vs. time for a subject under anesthesia for surgery.
Figure 4B:
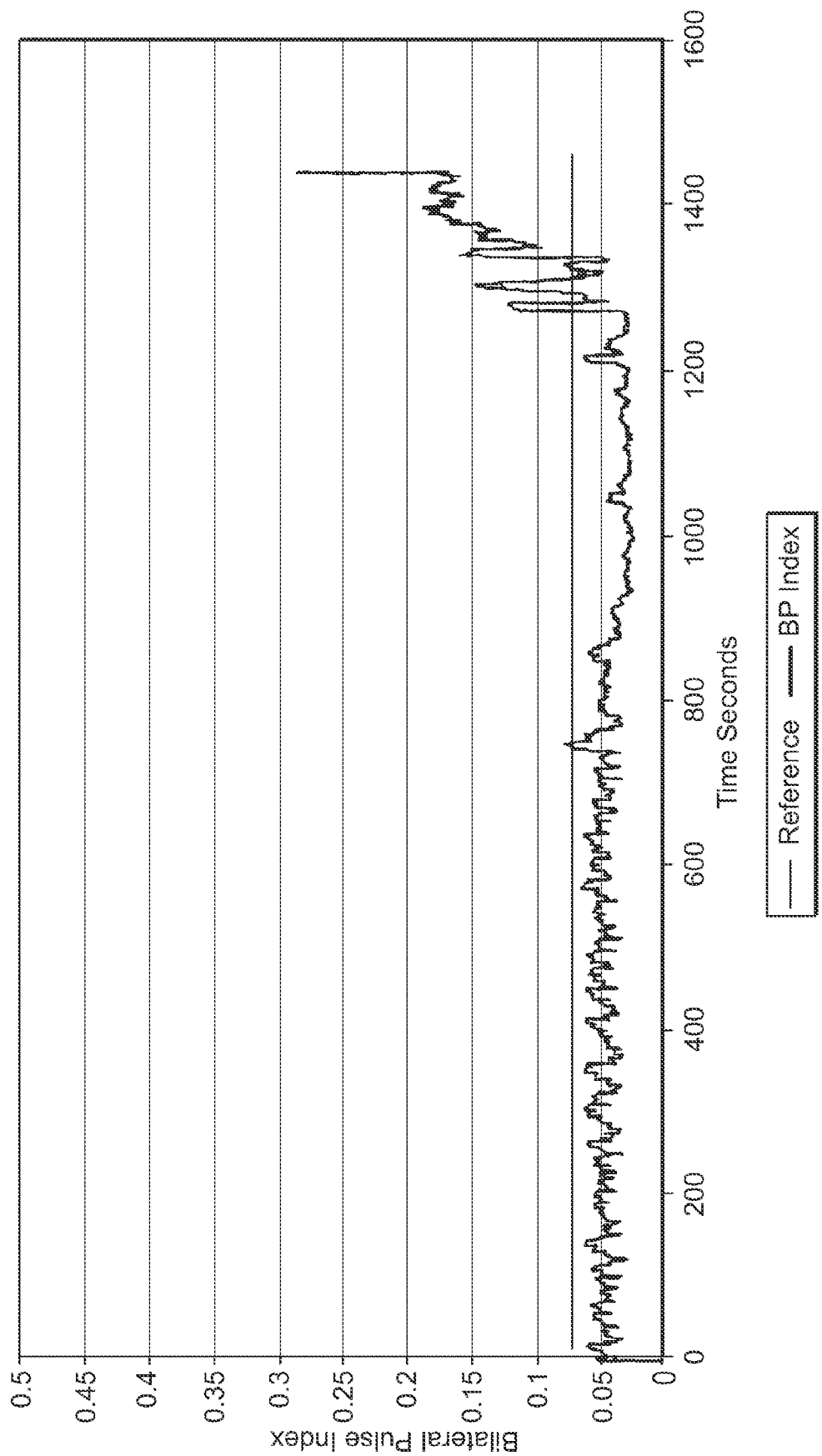

FIG. 4a shows BPI data for a subject who is undergoing an operation using a laser to remove a kidney stone. Note that the subject went under full anesthesia at approximately 100 seconds. A paralyzing drug was used during this operation. FIG. 4b shows the last portion of the operation started in FIG. 4a. The subject started out of anesthesia at about 1,300 seconds. FIGS. 4a and 4b describe a condition that might be considered "textbook" relating to successful anesthesia since the patient went under anesthesia and remained at a low level of mental activity during the entire operation.

The experiments described herein have shown that a clear and reliable signal is produced using the Bilateral Pulse method disclosed herein when a subject is asleep and/or under anesthesia. Electrical noise interference accounted for a major distortion of the data. Its removal is considered a routine engineering development both with software and electronic design.

It was also observed that the installation of the two sensors was very routine. No special positioning was necessary since the use of the CV method overcame these problems. The sensors were just clipped into position and the operation proceeded as usual.

It is recognized that modifications and variations of the present invention will be apparent to those of ordinary skill in the art and it is intended that all such modifications and variations be included within the scope of the appended claims.

What is claimed is:

1. Method for monitoring brain activity comprising:
   detecting with a sensor or sensors left and right cardiac pulse signals at bilateral locations on a body for a selected number of cardiac cycles;
   computing on a computing apparatus the standard deviation of the left and right pulse signals for the selected number of cardiac cycles;
   normalizing on the computing apparatus the standard deviation of the left and right pulse signals by dividing the left and right standard deviations by the mean of the left and right pulse signals, respectively, computed over the selected number of cardiac cycles to produce a left and a right Coefficient of Variation (CV) of the pulse signals; and
   generating a Bilateral Pulse Index (BPI) from the left and right Coefficients of Variation according to the equation BPI=((Left CV+Right CV)/2)+(Absolute (Left CV−Right CV)),
   wherein BPI relates to brain activity.

2. The method of claim 1 wherein the bilateral locations are left and right earlobes.

3. The method of claim 1 wherein the bilateral locations are left and right portions of a forehead.

4. The method of 1 wherein the bilateral locations are left and right carotid arteries at the neck.

5. The method of claim 1 wherein the brain activity is the sleep state.

6. The method of claim 1 wherein the brain activity is awareness under anesthesia.

7. The method of claim 1 wherein the pulse signals are detected by flesh penetrating electromagnetic radiation sensors.

8. The method of claim 1 wherein the pulse signals are detected by plethysmographic or oximeter sensors.

9. The method of claim 1 wherein the sensor or sensors are selected from the group consisting of optical sensors, RF displacement sensors, capacitance displacement sensors, pressure sensors, acoustic distance sensors, acoustic doppler flow sensors, optical displacement sensors, and ear canal sensors.

10. The method of claim 1 wherein the sensor or sensors are connected to the computing apparatus by cables that limit the introduction of motion artifacts during movement.

11. The method of claim 1 wherein the sensor or sensors form a two-channel instrument.

* * * * *